United States Patent
Mahajan (10) Patent No.: US 9,521,974 B2
(45) Date of Patent: Dec. 20, 2016

(54) URINE FLOW METER INCORPORATING A WEIGHT SENSOR WITH ARRANGEMENT OF SIPHONING AND SOLENOID VALVE TO START AND STOP RINSING OF URINE CONTAINER AUTOMATICALLY

(71) Applicant: Jayant Dattatraya Mahajan, Satara (IN)

(72) Inventor: Jayant Dattatraya Mahajan, Satara (IN)

( * ) Notice: Subject to any disclaimer, the term of this patent is extended or adjusted under 35 U.S.C. 154(b) by 56 days.

(21) Appl. No.: 14/381,211

(22) PCT Filed: Feb. 27, 2013

(86) PCT No.: PCT/IB2013/051551
§ 371 (c)(1),
(2) Date: Aug. 26, 2014

(87) PCT Pub. No.: WO2013/128376
PCT Pub. Date: Sep. 6, 2013

(65) Prior Publication Data
US 2015/0105694 A1    Apr. 16, 2015

(30) Foreign Application Priority Data
Mar. 2, 2012  (IN) .......................... 566/MUM/2012

(51) Int. Cl.
| | | |
|---|---|---|
| *G01F 3/38* | (2006.01) | |
| *A61B 5/20* | (2006.01) | |
| *G01F 9/00* | (2006.01) | |
| *G01F 1/00* | (2006.01) | |
| *E03D 13/00* | (2006.01) | |

(52) U.S. Cl.
CPC ............... *A61B 5/208* (2013.01); *G01F 1/007* (2013.01); *G01F 9/003* (2013.01); *E03D 13/005* (2013.01)

(58) Field of Classification Search
None
See application file for complete search history.

(56) References Cited

U.S. PATENT DOCUMENTS

| | | | |
|---|---|---|---|
| 4,554,687 A | 11/1985 | Carter et al. | |
| 5,176,148 A * | 1/1993 | Wiest ........................ | G01F 1/52 600/573 |
| 6,053,197 A * | 4/2000 | Gorges .................... | E03C 1/281 137/247.39 |
| 6,425,411 B1 * | 7/2002 | Gorges ...................... | E03C 1/28 137/247.39 |
| 6,750,773 B2 * | 6/2004 | Higgins ................. | E03C 1/281 200/61.04 |
| 7,811,237 B2 * | 10/2010 | Brohan .................. | A61B 5/208 600/584 |

FOREIGN PATENT DOCUMENTS

GB        2437549 A        10/2007

* cited by examiner

*Primary Examiner* — Harshad R Patel (57) ABSTRACT

The invention provides a urine flow meter of gravitation or capacitance type in which a container is connected to a weight transducer or a capacitance sensor. An arrangement is provided to sense the level of urine in the container. An arrangement of siphon tube & solenoid valve is also provided to start and stop rinsing of the container automatically. The invention is easily adapted to a male or female type urinal. The collected urine in beaker is flushed by siphon after completion of test.

13 Claims, 7 Drawing Sheets

Figure 1

*(PRIOR ART)*

Figure 2

*(PRIOR ART)*

Figure 3

*(PRIOR ART)*

Figure 4

(PRIOR ART)

URINE FLOW METER INCORPORATING A WEIGHT SENSOR WITH ARRANGEMENT OF SIPHONING AND SOLENOID VALVE TO START AND STOP RINSING OF URINE CONTAINER AUTOMATICALLY

FIELD OF INVENTION

This invention relates to urine flow meters. In particular, this invention relates to automatic discharge of urine from container of a urine flow meter after completion of passing of urine. The invention also relates to automatic flushing/cleaning of the (urine container) beaker & tubing system after every cycle of urine passing.

BACKGROUND OF THE INVENTION

The urethra is a tube that connects the urinary bladder to the genitals for the removal of fluids out of the body. If any constrictions or obstructions are formed in the urethra, the flow in urethra is reduced. Prostatic hyperplasia, which affects a significant proportion of male population, particularly at advanced stages of life, is one such condition.

According to one estimate (http://www.ennovations.co.uk/urine-flow-meter), Prostate disorders affect approximately 50% of the male population over 40 years old. Furthermore, around 24,700 men are diagnosed with prostate cancer each year in the UK. A regular urine flow test becomes a valuable tool in such instances to spot early signs of abnormalities.

There is currently a problem in timely and accurate diagnosis of the urodynamic obstruction. First small reductions in the urine flow often go unnoticed by patients. Second, due to variation in the patient awareness, reliance on patient awareness often produces distorted picture depending on the patient norm. In general, an urination peak flow rate of greater than around 15 ml/sec is considered normal for a man. A peak flow of less than 10 ml/sec has an 80% chance of being associated with urodynamic obstruction.

Current Devices for measuring the rate of flow of urine are cumbersome and require cleaning and maintenance. The hygiene awareness among patients and health workers is rising and the manual operations involving handling of urine containing vessels and equipment are considered unhygienic or undesirable according to modern hygiene norms.

Urine flow meters are used regularly to get urine flow rate, average urine flow rate, Peak urine flow rate & graph representing urine flow against time.

Figure 1:
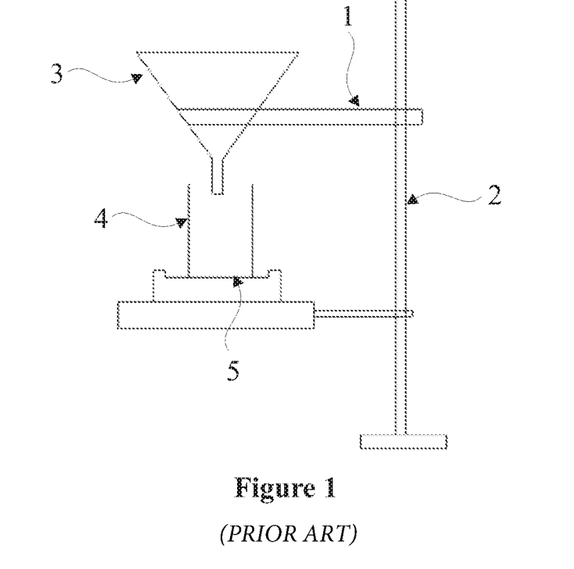
FIG. 1 shows a stand-up type existing urine flow meter
Figure 2:
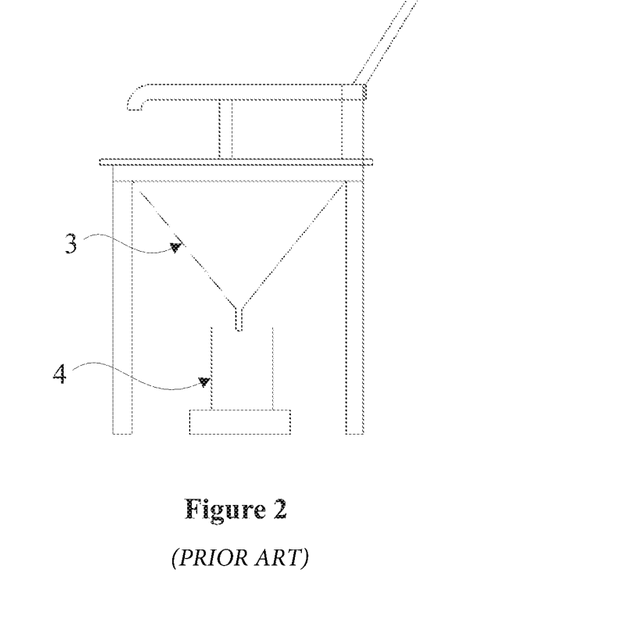
FIG. 2 shows a sitting type urine flow meter

Three types of urine flow meters are widely available. These are:
1 Rotating disk method
2 Gravimetric or Weight type
3 Capacitance type The present general arrangement for gravimetric or capacitance type urine flow meters is shown in FIG. 1 or FIG. 2. The patient is made to pass urine in funnel while standing (FIG. 1) or by sitting on commode type chair (FIG. 2). The patient urinates in a funnel and the urine is collected in a beaker which is taken away, emptied and rinsed clean. Also, because of the way the beakers are positioned in the currently available urine flow meters, the beakers are easily tilted spilling the urine on the floor, and more importantly on the sensors. The present urine flow meters are thus not very easy and hygienic to use, having the main disadvantage that the urine container has to be emptied & cleaned, by, either the patient or the attain dent.

There is a further problem with the present urine flow meters. The typical patient psychology is such that the urine flow of a patient possibly gets affected if the patient knows he is undergoing a specific test. It widely acknowledged by health professionals that the patient should be in his natural regular position while passing the urine to get his correct urine flow characteristics. However, the existing urine flow meters do not always provide natural conditions or environment in which a patient would be encouraged to urinate naturally. The instances of patient manipulating urine flow to mask the actual flow rates are common. The sight of large and unsightly flow meters can thus have an adverse impact on the urine flow related diagnosis.

With regards the patent literature available on the subject of uroflow meters, we have found a large body of works that suggest that there is a great room for improvement in this field. It is evident from a study of the number of patent applications available on the topic that the current ways of measuring the urinary flow rate has several limitations and drawbacks. Some of these are discussed here.

U.S. Pat. No. 5,176,148 by Weist et al, in relation to the West German Patent Specification No. 30,07,855 states that: 'A Uroflow measuring device of this class must also be able to be installed in the bathroom in the urological office, so that the urine can flow off directly. This permits only the use of a device which does not collect the urine. However, much greater importance is attached to accurate volume measurement in clinical urodynamic investigations. The urine is collected in a beaker at the measuring device. Furthermore, accurate representation of the flow curve as a function of time is very important for diagnosis. This is possible only when the flow is measured directly. When double differentiation is required for volume-based measurement to represent the increase in flow, the calculated result will be too inaccurate because of the effect of disturbances e.g., vibrations and wave movements of the liquid collected. Emptying of the collected liquid is too expensive in urological practice because of the great number of uroflow tests performed as a preliminary examination.'U.S. Pat. No. 6,750,773 by Higgins in relation to the waterless urinals, such as those disclosed in U.S. Pat. No. 6,053,197 and U.S. Pat. No. 6,425,411 states that: ' . . . such devices typically use a water trap in which a low density sealant layer covers a small amount of wastewater remaining in the urinal trap. Such urinals conventionally do not have a flush mechanism; therefore, some amount of wastewater will remain in the trap at all times. The sealant layer prevents odors from escaping from and through the wastewater. Any slow draining of wastewater from the trap or blocking within the trap or sufficient use of the urinal to cause the supply of sealant to be significantly diminished, will result in unpleasant odors. Therefore, it is important for such urinals to be cleaned and serviced regularly, and especially when draining slowly, and a need exists for determining when the conditions for cleaning and servicing pertain.'

Brohan in the U.S. Pat. No. 7,811,237 states that: 'uroflowmeters that existed at the time of that application required that the user direct his/her urine stream into a device and, thus, today's uroflowmeters can be uncomfortable, messy, and difficult for the patient to use. Furthermore, the use of uroflowmeters in hospitals and doctor's offices poses a risk to medical personnel of contacting urine excrements. Additionally, collecting data using today's commercially available portable uroflowmeters is still unpractical, available only to a limited number of patients producing only limited number of measurements.'

For these reasons, a need exists for improved systems for and methods of assessing urinary flow rate, in order to provide mechanisms for measuring urinary flow rate that are portable, convenient, easy to use in a non-stressful and risk-free environment and able to be used for mass examinations.

There is therefore a need to provide urine flow meters that are easy to use, preferably hidden from the patient sight, and hygienic to operate.

OBJECTS OF THE INVENTION

Accordingly, one of the objects of the invention is to provide a urine flow meter that is hygienic & easy to operate.

Another object of the invention is to provide a urine flow meter that is partially hidden from the patient's sight and provides a familiar environment of standard urinal.

SUMMARY OF INVENTION

The invention provides a urine flow meter of gravitation or capacitance type in which a container is connected to a weight transducer (5) or a capacitance sensor. An arrangement is provided to sense the level of urine in the container. An arrangement of siphon tube (8) and solenoid valve (11) is also provided to start and stop rinsing of the container automatically. The invention is easily adapted to a male or female type urinal. The collected urine in beaker (4) is flushed by siphon (8) after completion of test.

LIST OF PARTS

Support for funel-1
U-bracket-1a
Stand-2
Funnel-3
Beaker-4
Weight transducer-5
Capacitance transducer-5A
Processor-6
Printer-7
Siphon tube-8
Top level of siphon-9
Top level of beaker-9A
Maxinum bladder capacity-9B
Drainage coupler-10
Solenoid valve-11
Water tube for flushing-12
Flush water tank-13
Flow regulator mechanical valve-14
Water trough-15
Pump-16

DETAILED DESCRIPTION OF THE INVENTION

Figure 3:
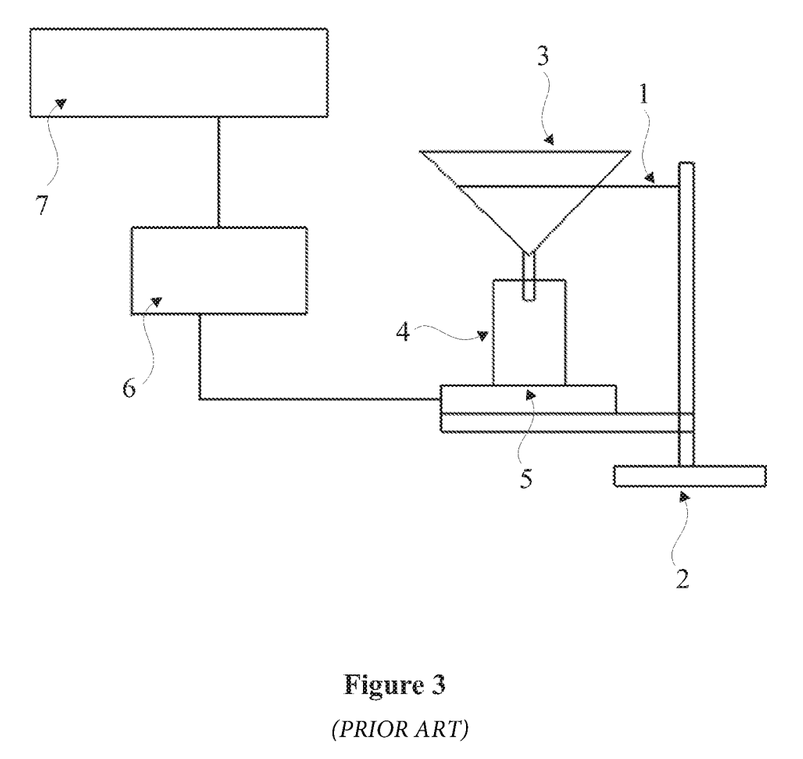
FIG. 3 shows a schematic of an existing urine flow meter
Figure 4:
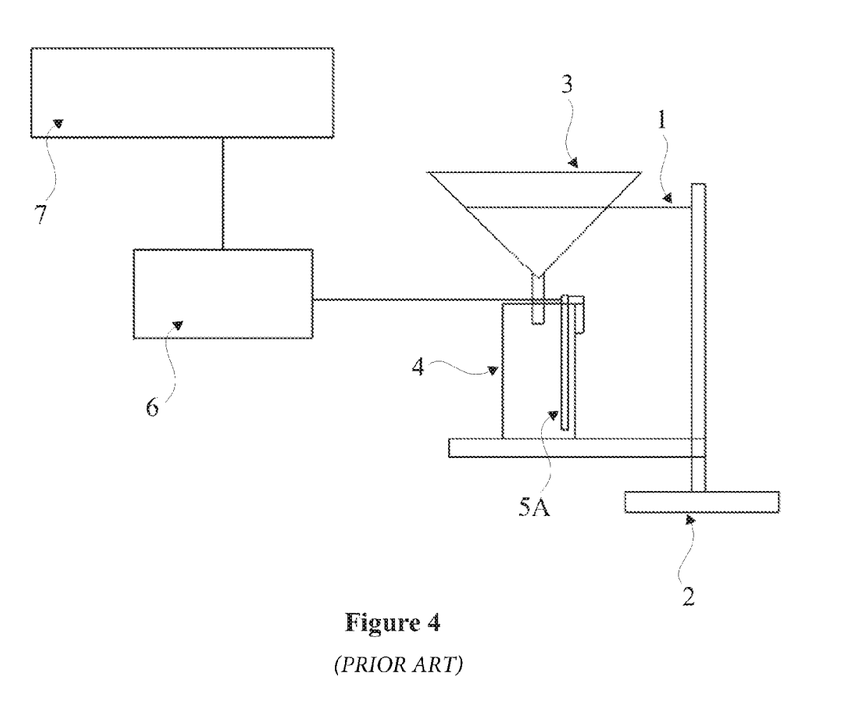
FIG. 4 shows a schematic of an existing capacitance sensor type urine flow meter

Some of the existing urine flow meters are shown in FIGS. 1 and 2. The patient urinates in funnel which is supported by a support which in itself is attached to a stand. The voided urine is collected in a beaker. Change in volume of the urine is traced by a weight transducer in case of gravimetric type urine flow meter (FIG. 3), and by capacitance sensor or transducer (FIG. 4). The transducer is typically supported by the same stand that supports the funnel. In the case of digitally or electronically operating urine flow meters, a data processing unit, which calculates the time and flow rates, is connected to the transducer and a printer is provided to print out the results.

Figure 5:
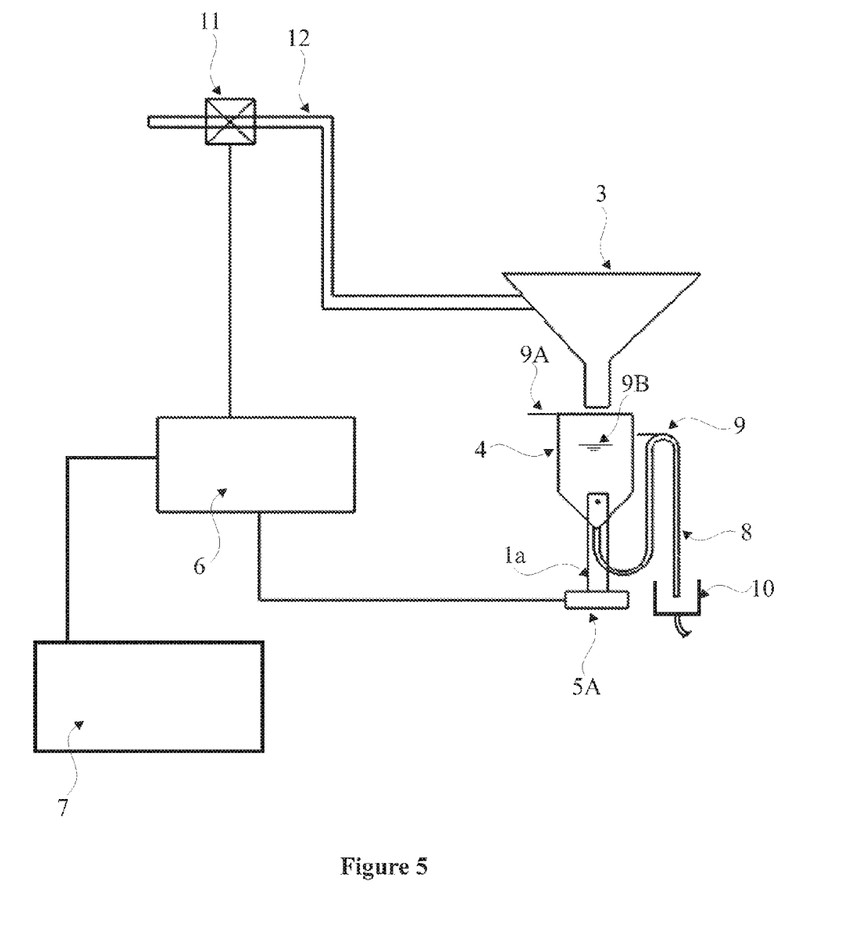
FIG. 5 shows a schematic of the urine flow meter of the invention

As shown in FIG. 5, the present invention uses a specially designed beaker (4), solenoid valve (11) and electronic processor (6) with relay to create auto flushing & cleaning weight type or capacitance type urine flow meter.

Figure 5A:
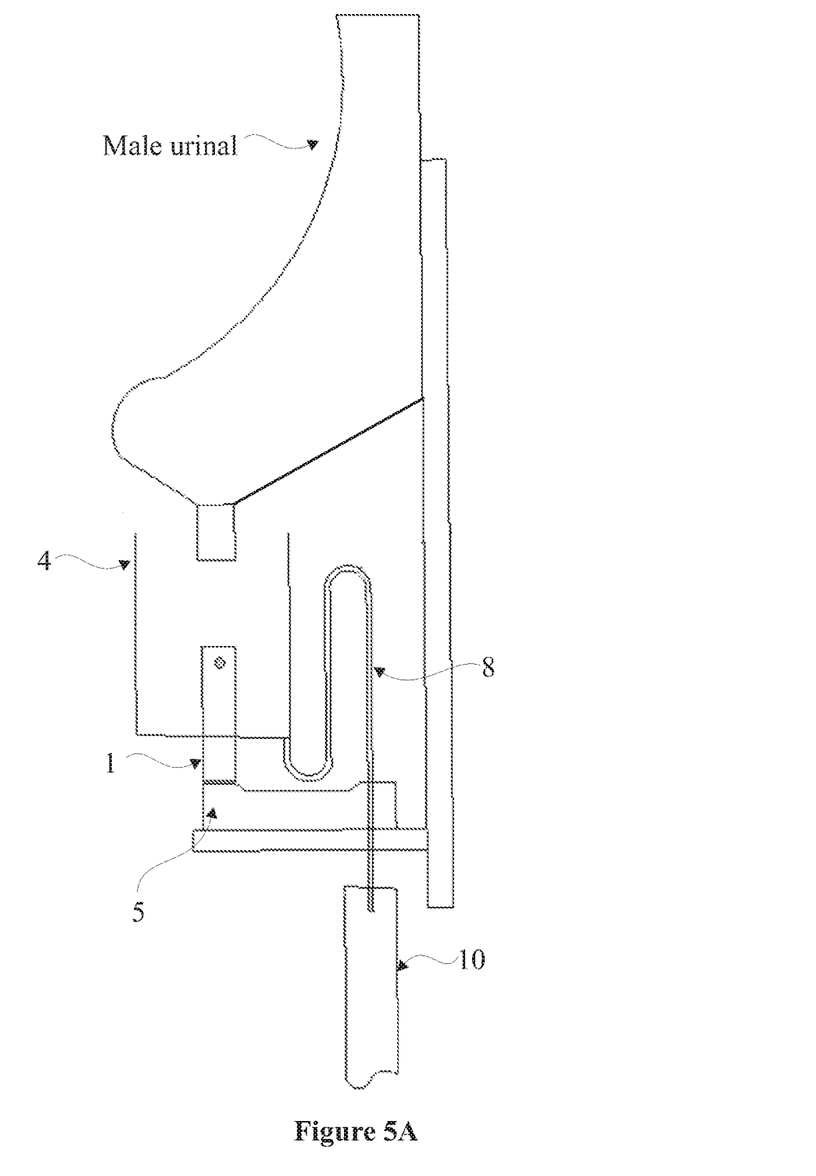
FIG. 5A shows invention adapted for male urinal
Figure 5B:
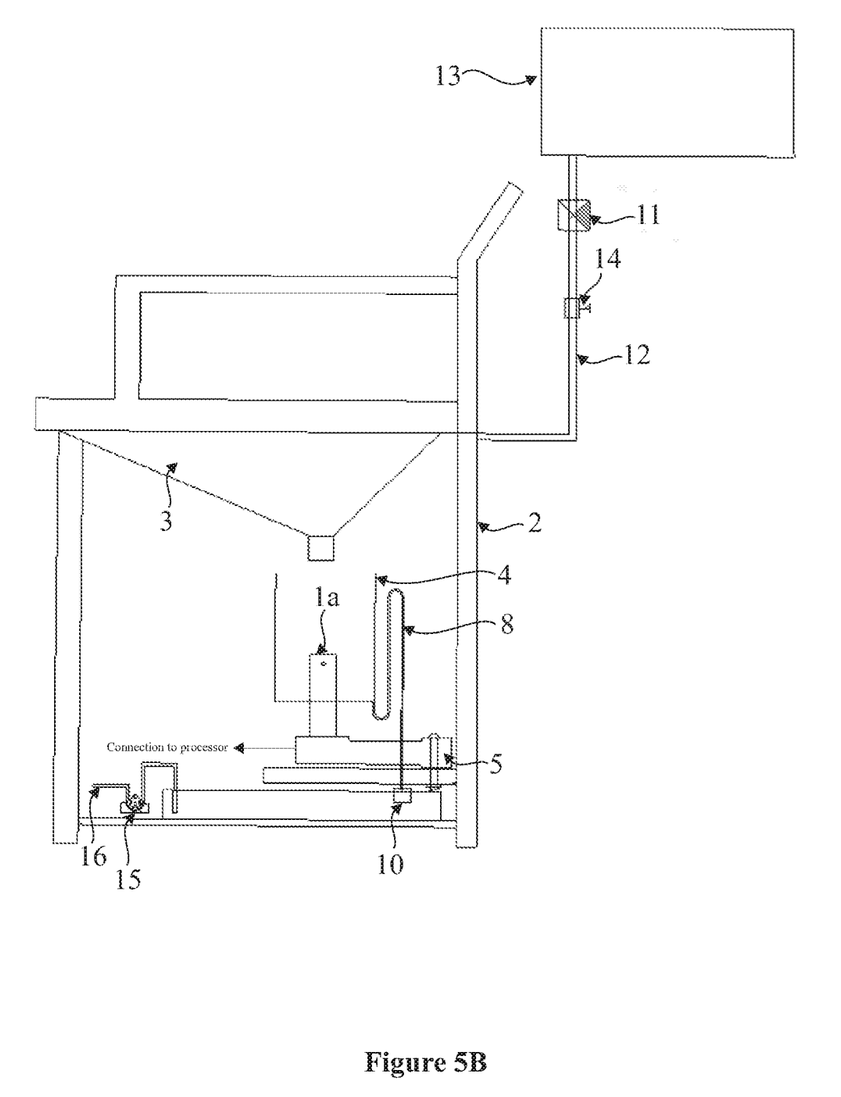
FIG. 5B shows invention adapted for uro flow with chair.

As shown in FIGS. 5A and 5B, the beaker (4) is provided with arrangement to receive urine from the cistern of the typical urinal for male and female type urinals respectively. The beaker (4) is also provided with a siphoning device in the form of a tube. One end of the siphon tube (8) is connected to the beaker (4) at its lower end. The other end of the siphon tube (8) hangs loose over a drainage coupler (10). It is important that the siphon tube (8) does not touch the drainage coupler (10). The highest level of the siphon tube (8) is set so that the urine level inside the beaker (4) does not exceed a predetermined level. The highest level of siphon tube (8) is thus typically above the level achieved by urine contained in a human bladder of a maximum capacity of, say, 1000 ml. The predetermined level set so that before the siphoning begins, the beaker (4) holds a certain volume termed as pre-siphon volume. The pre-siphon volume is set at any desired level and is adjustable with the use of beakers of suitable size. The pre-siphon volume should exceed the bladder capacity of the person using the urine flow meter.

A mechanical flow regulator valve is provided in between the solenoid valve (11) and exit end of water pipe at the urinal pot, to adjust the rate of flow of water discharge to urinal. This is important as this allows siphon tubes of various flow capacities and beakers of various sizes to be used in the invention. Unless such mechanical flow regulator valve is provided, it would be impossible to ensure that the beaker (4) does not overflow. At the time of the installation of the invention, the flow rate is set using the mechanical flow regulator valve at a value that ensures that there is a balance between the flow through the siphon tube (8) and the incoming flushing fluid used during the flushing cycle.

The beaker (4), along with the siphon tube (8), is mounted weight sensor (or transducer) with the help of a U-bracket (1a).

One of the most important features of the invention is that entire weight of the device is accounted for during the urine flow measurement and calculation. As the free end of the siphon tube (8) hangs loose without touching any objects other than the beaker (4), there is no unknown or unaccounted-for weight which could affect the accuracy of the urine flow measurements.

A flushing arrangement is provided so that the entire equipment is rinsed without having to remove the beaker (4). A relay processor and a solenoid valve (11) are provided to facilitate the flushing and rinsing operation. Any number of rinsing cycles may be programmed and operated.

The urine will be discharged gravitationally to a drainage system in normal circumstances, but in the case natural gravitational discharge is not possible, a urine and water collection trough (15) is provided below the siphon tube (8) end (see FIGS. 5, 5A, 5B) such that no part of the trough (15) will touch the siphon tube (8). Further, a tube pump (16) (peristaltic) is optionally provided to empty the trough (15) and discharge the urine/water forcefully in drainage system.

The flow measurements are captured electronically or digitally.

The beaker (4), siphon tube (8) and the U-bracket (1a), the weight sensors are all tucked away behind a façade so that the patient is unaware of their presence.

In the case where a malfunctioning of the device becomes apparent during its operation, an alarm which is operable by the patient is provided.

Adaptation of the present invention to male and female (chair type) type urinals is now disclosed. As shown in FIG. 5A, in the case of a stand-up type male urinal, the urinal cistern is so positioned that the urine is collected directly into the beaker (4). The assembly of the beaker (4), the siphon tube (8), the bracket U-(1a) and the weight transducer (5) is mounted preferably such that it is hidden behind a façade. The solenoid valve (11) and the relay processor (6) receive signals from the weight transducer (5) and are connected to the flush water system so that the urinal and the beaker (4) are flushed when required.

In the case of a chair type urinal (see FIG. 5B), a tube is optionally connected between the outlet of the urinal and the beaker (4).

OPERATION OF THE INVENTION

Figure 6:
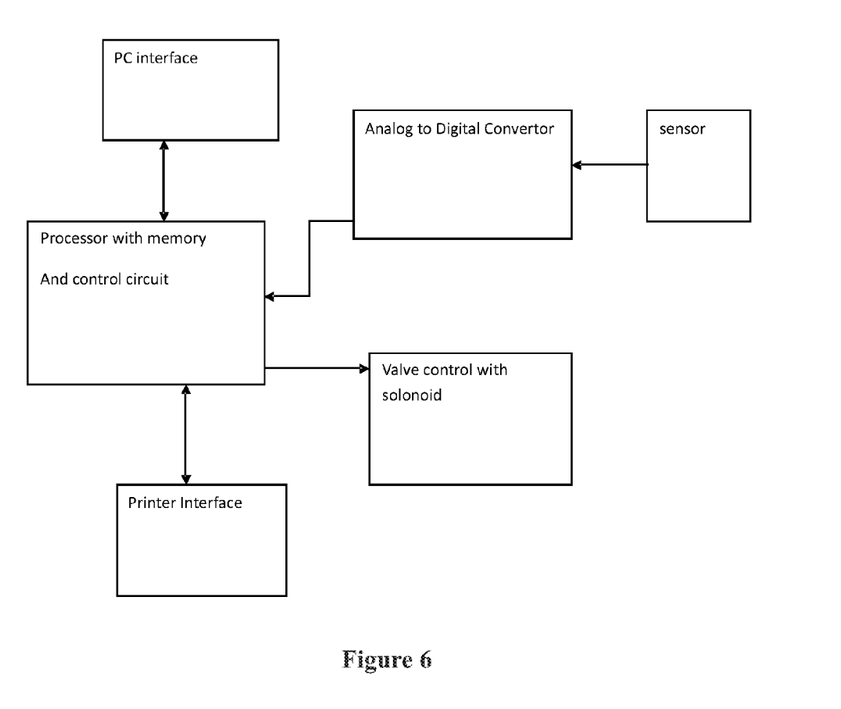
FIG. 6 shows a block diagram of hardware used in the present invention

FIG. 6 shows a block diagram of the various controls used in the present invention. The sensor of the urine flow meter is connected to an analog-to-digital converter, which sends a signal to the processor unit with the control circuitry. The processer unit sends signals to the solenoid valve (11) which controls the water flow to the urine flow meter. The processor unit is also connected to a printer (7) interface and a PC interface.

As the patient starts to urinate in toilet to which the equipment of the invention is attached, the urine is collected in beaker (4) though the funnel (3) of the urinal. The design of the funnel (3) is such that no traces of urine remain on it.

The change in weight and volume of the urine during the urination is registered by the processor (6) through the signals sent by the weight transducer (5). Also measured are the time at starting and stopping of urination. Once the urine flow meter determines that, based on the information provided by its sensors and the built-in electronic logic, the urination has stopped, a predetermined period, preferably 10-45 seconds, more preferably 30 seconds, is provided after which the relay processor operates the solenoid valve (11) and releases water for flushing the toilet and rinsing the flow meter apparatus.

As the water starts to enter the funnel (3) and subsequently into the beaker (4), the volume and the level of liquid in the beaker (4) start to rise. As the water level in the beaker (4) starts to rise and reaches the top level of the siphon tube (8), it starts pouring out of the other end of the siphon tube (8) into the drainage coupler (10). Initially, a mixture of urine and flush water is drained out. However, once all urine has been washed away in this manner, a predetermined quantity of flush water is sent through the system to ensure complete rinsing. Though the siphon system ensures that there will not be overflowing of the beaker (4), in normal circumstances, as a precaution the solenoid (11) is closed at certain volume of liquid in beaker (4), which is typically more than volume of beaker (4) at the level of the upper tip of the siphon tube (8) & less than the total volume of beaker (4).

A flow regulator mechanical valve (14) is provided to regulate flow of water as per standard values, and ensures that the beaker (4) does not overflow during the flushing cycles.

The various advantages of the present invention are apparent from the foregoing discussion. These are:

The siphon system ensures that there is no flow out of the system during the act of urination and that all features such as start and stop time of urination including the hesitancy period, peak and average flow are captured. The automated flushing or rinsing system ensures that there is no spillage of urine during the entire operation.

Since the apparatus is attached to a male stand-up urinal, it provides a natural urination position and environment.

As the beaker (4) containing urine does not need to be handled manually, the urine flow meter of the invention provides a more hygienic piece of equipment than the currently available urine flow meters.

As there is automated and regular flushing and rinsing of the urine flow meter, there is no lingering foul smell As there's no need to manually emptying and cleaning the equipment the human resources required are reduced, leading to operational economy It is evident from the foregoing description that the present invention has several embodiments as follows.

1. A uroflow meter comprising a beaker (4), a solenoid valve (11) and electronic processor (6) with relay and control circuitry and a weight sensing sensor, characterized in that said beaker (4) is provided with an arrangement to receive urine from the cistern of the typical urinal, and also a siphoning device in the form of a tube; one end of the siphon tube (8) being connected to said beaker (4) at the lower end of said beaker (3), and the other end of said siphon tube (8) positioned to release the contents of the beaker (4) into a drainage system; said siphon tube (8) securely positioned such that any part of it does not touch any part of the drainage system; said weight sensing sensor connected to said beaker (4) and also to an analog-to-digital converter such that when urination begins into the beaker (4), said sensor sends a signal to said converter which calculates the rate of urination 2. A uroflow meter as described in embodiment 1, wherein said solenoid valve (11) is so designed that after first time period following the stoppage of urination, it releases a first quantity of flushing fluid into said beaker (4), said flushing fluid being drained away completely by said siphon tube (8), thereby completing a flushing cycle.

3. A uroflow meter as described in embodiments 1 and 2, wherein the number of flushing cycles is greater than one.

4. A uroflow meter as described in embodiments 1 to 3, wherein said typical urinal is of male or female type.

5. A uroflow meter as claimed in claims 1 to 4, wherein the solenoid of said solenoid valve (11) is closed at a first volume of liquid in beaker (4), said first volume being more than volume of beaker (4) at the level of the upper tip of the siphon tube (8) but less than the total volume of beaker (4).

6. A uroflow meter as described in embodiments 1 to 5, wherein said drainage system works on a gravitational principle.

7. A uroflow meter as described in embodiments 1 to 5, wherein said drainage system is in the form of a drainage trough provided with a pump (16) to drain away collected urine from said drainage trough, said pump (16) being operated by a processor (6) and a relay.

8. A uroflow meter as described in embodiments 1 to 7, wherein said first time period is 10-45 seconds, preferably 30 seconds.

9. A uroflow meter as described in embodiments 1 to 8, said meter further comprising a mechanical flow regulating valve to regulate the flow of flushing fluid into the beaker (4) during the flushing cycle.

10. A method to measure urination flow said method comprises the steps of
    a. providing a uroflow meter as described in embodiment 1
    b. starting the flow of urine into said beaker (4)
    c. waiting for a first time period from the stoppage of urination
    d. flushing said beaker (4) with flushing fluid, said flushing fluid preferably being clean water and released using a solenoid valve (11), using a desired number of flushing cycles.

11. A method to measure urination flow as described in embodiment 10, wherein said number of flushing cycles is greater than one.

12. A method to measure urination flow as described in embodiments 10 and 11, wherein said solenoid valve (11) is closed at a first volume of liquid in beaker (4), said first volume being more than volume of beaker (4) at the level of the upper tip of the siphon tube (8) but less than the total volume of beaker (4).

13. A method to measure urination flow as described in embodiments 10 and 11 wherein the rate of flushing fluid into said beaker (4) is regulated by a mechanical flow regulating valve (14).

14. A method to measure urination flow as described in embodiments 10 to 13 wherein said drainage system works on a gravitational principle.

15. A method to measure urination flow as described in embodiments 10 to 13, wherein said drainage system works by collecting the urine into a drainage trough from where it is further drained away using a pump (16) which is operated by a processor (6) and a relay.

While the above description contains much specificity, this should not be construed as limitation in the scope of the invention, but rather as exemplification of the preferred embodiments thereof. Many other variations are possible. Accordingly, the scope of the invention should be determined not by the embodiments illustrated, but by the appended claims and their legal equivalents.

The invention claimed is:

1. A uroflow meter comprising a beaker (4), a solenoid valve (11) and electronic processor (6) with relay and control circuitry, and a mechanical flow regulating valve (14) that is placed on a flushing tube (12) that connects a flush tank (13) and the funnel (3) to receive urine, the urine received in said funnel (3) being emptied into said beaker (4), and said solenoid valve (11) being connected to said mechanical regulating valve (14), characterized in that said beaker (4) is provided with an arrangement to receive urine from the cistern of a typical urinal, and also a siphoning device in the form of a tube; one end of the siphon tube (8) being connected to said beaker (4) at the lower end of said beaker (4), and the other end of said siphon tube (8) positioned to release the contents of the beaker (4) into a drainage system; said siphon tube (8) securely positioned such that the top tip of the siphon tube (8) is at such height that the volume of the beaker at that level is more than 1000 ml and that any part of it does not touch any part of the drainage system; further characterized in that a weight sensing sensor is connected to said beaker (4) and also to an analog-to-digital converter such that when urination begins into the beaker (4), said weight sensing sensor sends a signal to said converter which calculates the rate of urination, and said weight sensing sensor senses stoppage of urine voiding, sends a signal to the electronic processor which in turn operates the solenoid valve after predetermined period of time for flushing the urinal.

2. The uroflow meter as claimed in claim 1, wherein said solenoid valve (11) is so designed that after a first time period following the stoppage of urination, it releases a first quantity of flushing fluid into said beaker (4), said flushing fluid being drained away by said siphon tube (8), thereby completing a flushing cycle.

3. The uroflow meter as claimed in claim 2, wherein the number of flushing cycles is greater than one.

4. The uroflow meter as claimed in claim 3, wherein said typical urinal is of male or female type.

5. The uroflow meter as claimed in claim 4, wherein the solenoid of said solenoid valve (11) is capable of being closed at a first volume of liquid in said beaker (4), said first volume being more than a volume of said beaker (4) at a level of an upper tip of the siphon tube (8) but less than the total volume of said beaker (4).

6. The uroflow meter as claimed in claim 5, wherein said drainage system works on a gravitational principle.

7. The uroflow meter as claimed in claim 6, wherein said drainage system is in the form of a drainage trough provided with a pump (16) to drain away collected urine from said drainage trough.

8. The uroflow meter as claimed in claim 7, wherein said first time period is 10-45 seconds, preferably 30 seconds.

9. A method to measure urination flow said method comprises the steps of a. providing a uroflow meter as claimed in claim 7, b. starting the flow of urine into said beaker (4), c. waiting for a first time period from the stoppage of urination, and d. flushing said beaker (4) with flushing fluid, said flushing fluid preferably being clean water and released using a solenoid valve (11), using a desired number of flushing cycles.

10. A method to measure urination flow said method comprises the steps of a. providing a uroflow meter as claimed in claim 6, b. starting the flow of urine into said beaker (4), c. waiting for a first time period from the stoppage of urination, and d. flushing said beaker (4) with flushing fluid, said flushing fluid preferably being clean water and released using a solenoid valve (11), using a desired number of flushing cycles.

11. A method to measure urination flow said method comprises the steps of a. providing a uroflow meter as claimed in claim 5, b. starting the flow of urine into said beaker (4), c. waiting for a first time period from the stoppage of urination, and d. flushing said beaker (4) with flushing fluid, said flushing fluid preferably being clean water and released using a solenoid valve (11), using a desired number of flushing cycles.

12. A method to measure urination flow said method comprises the steps of a. providing a uroflow meter as claimed in claim b. starting the flow of urine into said beaker (4), c. waiting for a first time period from the stoppage of urination, and d. flushing said beaker (4) with flushing fluid, said flushing fluid preferably being clean water and released using a solenoid valve (11), using a desired number of flushing cycles.

13. The method to measure urination flow as claimed in claim 12, further comprising repeating step d.

\* \* \* \* \*